United States Patent [19]
Claessens

[11] Patent Number: 6,045,226
[45] Date of Patent: Apr. 4, 2000

[54] DEVICE FOR MEASURING THE VISUAL ATTENTION OF SUBJECTS FOR A VISIBLE OBJECT

[75] Inventor: Dominique Paul Gerard Claessens, Geneva, Switzerland

[73] Assignee: Eyelight Research N.V., Willemstad, Netherlands

[21] Appl. No.: 09/155,056

[22] PCT Filed: Apr. 14, 1997

[86] PCT No.: PCT/NL97/00186

§ 371 Date: Sep. 23, 1998

§ 102(e) Date: Sep. 23, 1998

[87] PCT Pub. No.: WO97/38622

PCT Pub. Date: Oct. 23, 1997

[30] Foreign Application Priority Data

Apr. 12, 1996 [NL] Netherlands ............................ 1002855

[51] Int. Cl.[7] ...................................... A61B 3/10
[52] U.S. Cl. ............................................ 351/205
[58] Field of Search .................... 351/205, 209, 351/210, 211; 606/4, 5; 600/558; 345/156, 158; 348/2; 382/117

[56] References Cited

U.S. PATENT DOCUMENTS

| 4,848,340 | 7/1989 | Bille et al. ................................ 606/4 |
| 4,931,865 | 6/1990 | Scarampi ................................. 348/2 |
| 5,325,133 | 6/1994 | Adachi ................................... 351/209 |

*Primary Examiner*—George Manuel
*Attorney, Agent, or Firm*—Foley & Lardner

[57] ABSTRACT

In order to measure the visual attention of persons or animals to a visible object, a beam (9) is radiated to an area of observation (1) including the persons or animals under test. A measuring arrangement in close vicinity to the object comprises a radiation source (1) emitting, e.g. an invisible parallel beam (9), a scanning member (3), guiding said radiation beam (9) across the area of observation (1) and detector means (6, 7) receiving the radiation scattered from the area of observation (1). Radiation from the retina and/or cornea of said persons or animals is selectively detected and transformed into an evaluation signal.

25 Claims, 4 Drawing Sheets

DEVICE FOR MEASURING THE VISUAL ATTENTION OF SUBJECTS FOR A VISIBLE OBJECT

The invention relates to a method as well as a device for measuring the visual attention of persons or animals for a visible object. Here, the term "object" should be interpreted in a broad sense. Thus, it comprises, among other things, material objects, such as products placed in shops or department stores, museum and exhibition works, e.g. with a view to the protection thereof, security apparatus, in order to determine whether there is a suspicious interest for said items, etc. Further, advertising in the most general sense, e.g. advertisement programmes, commercials, posters, advertisement bills, billboards, etc. Furthermore, it comprises "living objects", both human beings and animals, in which the attraction exerted on them must be measured.

In research of consumer behaviour, one generally employs methods and devices, through which no data can be produced without active cooperation of the respondent. It is true, that selected testees or respondents are of course willing to cooperate, but such a method has the disadvantage, that one is fully dependent on the faultless cooperation of the respondents. That is the reason why the results are not reliable.

For evaluating the marketability of a product placed in a department store, videocameras recording potential customers are used. From the recorded images it is determined to what extent the product to be evaluated attracts the attention of the public. Here, a disadvantage is that the use of videocameras infringes the privacy of arbitrary spectators, and that furthermore evaluating the recorded images is time-consuming and inaccurate.

According to the invention, a method has been developed for measuring the visual attention of persons or animals for a visible object, in which all of the above disadvantages have been avoided.

The method according to the invention is characterized in that from the vicinity of the object, a radiation beam is sent out to an observation area, where persons or animals are present, and that radiation reflected at the retina of the eyes is selectively detected and is transformed into an evaluation signal.

Since visible radiation might have a disturbing influence on the public, non-visible radiation is preferable. The method according to the invention at one hand has the advantage, that no active cooperation of respondents is required, yet only passive cooperation of arbitrary persons or animals, through which reliable information can be provided. Furthermore, there is no infringement of privacy, since only reflections of the eye are the standard for the measurement.

The invention efficiently employs the principle of retro-reflection at eyes, known per se, which can be realized in many ways and occurs when taking pictures with flashlight, among other things. When a person or animal turns his eyes to the flashlight, the light reflected at the eyes will be caught by the camera objective and cause (over)exposure at the position where the eyes fall on the film image of the camera. With the invention, this retro-reflection is efficiently employed, in order to determine, whether or not a person or animal present in a chosen area of observation is looking at the object to be evaluated.

According to the invention, it is possible to realize the evaluation in such a way, that the area of observation is covered by radiation which is received by suitable receiving systems.

However, it is also possible to employ a scanning beam covering the area of observation stepwise. With this method, the method is characterized in that the radiated beam is a substantially parallel beam being led scanningly across the area of observation, and that e.g. radiation reflected coaxially with the scanning beam is selectively detected and is taken as a standard for radiation reflected at the retina of eyes.

The radiation reflected coaxially with the scanning beam will then be said radiation retro-reflected at the pupil of the eye.

However, it is also possible to work with the radiation reflections on the cornea. With this method, the invention is characterized in that the radiation transmitted from the source of radiation and/or recording unit positioned near the object, reflected on the cornea of human being or animal, is received by the recording unit.

The recording unit, with or without amplification of radiation, must have a sensitivity and/or resolution high enough to determine the reflections. The resolution can be enhanced with the help of a device in such a way that a number of times per time unit, the sensor receives a part of an image being large enough. Enlarged recording of parts of an image can take place in a number of ways, e.g. with the help of a device by which a number of image portions are displayed, whether or not simultaneously, on said sensor in combination with a selection device, as a result of which a portion can always be measured individually.

The recording systems can be effected in many ways. By detectors, for example, including photo detectors; sensors including CCD sensors; detectors and sensors in combination with a display device, including optics; ultra-sensitive systems, including cameras, video cameras, etc.; systems having spectral sensitivity and/or resolution, including colour-sensitive or color-distinguishing cameras; combinations of different types of detectors and sensors functioning simultaneously or in a certain sequence, and each partly contributing to the evaluation signal. The sources or radiation can also be realized in many ways. For example, by means of light sources for visible light, UV or infrared light; sources of other types of radiation, including radar, sonar or centimeter waves; monochrome or spectral sources; coherent or non-coherent sources; modulated, continuous, of pulse sources; spatial or point sources.

The radiation beam too, can be realized in many ways. For example, diverging, converging, focussed, collimated or diffuse.

In all cases, by way of the information obtained, it can be determined, e.g. through coaxial retroreflection at the retina, whether or not persons watched the object to be evaluated. It goes without saying, that whatever the circumstances, it is required that the beam is, at least virtually, is emitted from the vicinity of the object, so that looking in the immediate surroundings of the object will mean that the person is actually watching the object.

For effecting the method, in which the area of observation is scanned by a parallel beam, the invention provides for a device, characterized by a radiation source having a substantially parallel beam, a scanning member, scanningly guiding said beam over the area of observation, a detector member, arranged such, that it receives the radiation reflected in the direction of the incident radiation in the area of observation and e.g. distinguishes coaxial radiation from non-coaxial radiation.

Efficiently, the invention can be such, that the detector member has a beam separator, consisting of a reflector unit mounted therein, arranged at an angle of e.g. 45° in relation to the beam path of the reflected radiation and being provided with a central passage for passing coaxial radiation, for example, and two detectors, mounted for receiving the passed radiation and the radiation reflected by the deflection member, respectively, and that the respective outputs of the two detectors are connected to respective inputs of a subtracting member. The subtracting member can be realized in many ways, e.g. by means of a differential amplifier. A differential amplifier, representing a substracting circuit substracting the output voltage signals of the two, is very advantageous and provides a signal, in which the non-coaxial radiation, which is in fact the background noise, is substantially eliminated. After all, this background noise is also present in the e.g. coaxially passed radiation, and by substracting said two signals, the pure e.g. coaxial radiation remains, which is the actual standard for retroreflection at the retina in the area of observation.

With a view to the positioning of the detector member, it is preferable, that a partly transmitting deflection member is mounted at an angle of e.g. 45° in the radiation path between radiation source and scanning member, said deflection member deflecting the returning reflected radiation towards said detector member.

Basically, the signal obtained at the output of the differential amplifier can be further analysed by computer means. It is also possible, to connect the output of the differential amplifier to the one input of a comparator circuit, with a reference being connected to the other input, which represents a condition, property or threshold value for eyes whether or not looking at the object to be evaluated. Further, as source of radiation, one could efficiently employ a source having a non-detectable low power radiation. Low power is desired, since a source of radiation which is too strong, might cause damage to eyes.

In order to apply the first method, in which all of the area of observation is irradiated by a beam, the invention provides for a device characterized by a recording unit for receiving radiation reflected at the area of observation, a pulse radiation system sychronized to the recording system for pulse-wise irradiation of the area of observation, and means for distinguishing signals recorded by the recording system from radiation reflected at the retina of eyes of persons or animals being in the area of observation.

By the fact, that the retroreflected radiation at the pupils of the eyes, looking in the direction of the object, is considerably stronger than the remaining, non-coaxial reflection, these pupils become significant on the recordings, in which coaxially reflected radiation is recorded (so-called "brightness pupils"), for example. This offers a number of possibilities for evaluating suitable viewing information from it.

There are number of possibilities for effecting such a device. Thus, the device can be designed such, that the recording system consists of one recording unit, and the pulse radiation system consists of one source of radiation having its pulse time synchronized with the recording time of the recording system, and that the pulse source is arranged transversely to the radiation path between recording optics and area of observation, a partly transmitting deflection member being positioned in said radiation path, said deflection member deflecting the radiation of the source of radiation in the direction of the radiation path to the area of observation.

In this embodiment, both background radiation and e.g. coaxial radiation (brightness pupils) will be combined in each image recording. In order to clearly distinguish the brightness pupils, it is preferred that the recording system is a colour recording system, that the pulse source is a source of soft, detectable radiation, and that there are means for analysis of the recorded spectral images. After all, the brightness pupil images represent predominantly the red component in the recording, and by an analysis of the red of the recordings, which can take place easily with the help of suitable computer means, it can be deducted, to what extent persons watched the object to be evaluated.

Another embodiment of the device according to the invention is characterized in that the recording system consists of one recording unit, and the pulse system consists of a first and a second pulse source, having their pulse times alternately synchronized with the recording time of the recording system, that the first pulse source is arranged next to the recording system for irradiating the area of observation with radiation, which is not coaxial to the radiation path between recording optics and area of observation, and that the second pulse source is arranged transversely to said radiation path, in which a partly transmitting deflection member has been positioned, which deflects the radiation of the second pulse source in the direction of the radiation path to the area of observation, and that there is a substracting circuit, coupled to the output of the recording system, said substracting circuit subtracting subsequently recorded image signals.

With this embodiment, the recording system alternately makes recordings of images caused by the first pulse source and images caused by the second pulse source. However, since no or hardly any coaxial retroreflection is possible with irradiation by the first pulse source, recordings are made without brightness pupils in them. On the other hand, the second pulse source is capable of sending pulses, the reflected radiation thereof e.g. also containing coaxial retroreflection, to the area of observation. Therefore, with the help of the second pulse source, recordings also containing the brightness pupils of viewers are made. By subtracting the images with and without the brightness pupils from each other in the subtracting circuit, one finally obtains image signals which contain only the brightness pupil data, and can be taken as a measure for the number of people or animals viewing.

Another possibility for a device according to the invention is characterized in that the recording system has a first and a second recording unit, arranged at a short distance from each other in such a way, that the radiation path between the area of observation and the first recording system is slightly shifted in relation to that which is between the area of observation and the second recording unit, that the recording system has one pulse source, its pulse time being synchronized wiht the recording time of the first and second recording unit, and arranged transversely to the radiation path between area of observation and first recording system, and that a partly transmitting deflection member is mounted in said radiation path, said deflection member deflecting the pulse source radiation in the direction of the radiation path to the area of observation, and that the outputs of the first and second recording unit are connected to the respective inputs of a subtracting circuit.

In contrast to the previous embodiment, with this embodiment, not the pulse radiation as such, but the arrangement of the two recording units is responsible for the selection in images with and without brightness pupils. With this arrangement, only the radiation of the first recording unit is capable of e.g. receiving coaxially reflected radiation, and by substracting the outputs of both recording units from each other in a subtracting circuit, just like in the previous case, again an image signal can be obtained, which is exclusively indicative of the retroreflection of persons viewing the object to be evaluated.

Yet another embodiment of the device according to the invention is characterized in that the recording system has a first and a second recording unit, and the pulse system consists of a first and a second pulse source, that the first pulse source is synchronized with the first recording unit, and the second pulse source is synchronized with the second recording unit, in such a way, that alternately the first camera records radiation of the first pulse source reflected from the area of observation and the second recording unit records radiation of the second pulse source reflected from the area of observation, in which the first pulse source is positioned non-coaxially in relation to the recording system arrangement and provides a radiation beam, which is not reflected coaxially from the area of observation to the first recording unit, and the second pulse source e.g. is positioned coaxially in relation to the recording system arrangement and provides a radiation beam, which is e.g. reflected coaxially from the area of observation to the second recording unit, and that the outputs of the first and second recording units are connected to the respective inputs of a subtracting circuit.

The essence of this embodiment is that there are two viewing systems, which do not see each other, one of them being able to detect retroreflections and the other one not.

In this case too, a clear image of the recorded brightness pupils can be achieved by subtracting the two images from each other.

The invention will now be explained further by means of the drawing. In the drawing.

As stated before, the invention is based on the principle of retroreflection at the eyes of persons or animals viewing. Retroreflection means, that the radiation incident on eye pupils is reflected in the same direction as the one in which it incides. When the incident radiation actually or virtually comes from an object to be evaluated, the retroreflection will naturally be a standard for the fact, whether a person or animal in a certain area of observation is looking in the direction of the incident radiation and thus also in the direction of the object. By providing for, that a detector is positioned in such a way, that said retroreflected radiation can be collected, it is possible to measure the attention of persons or animal in a certain area of observation from it.

Figure 1:
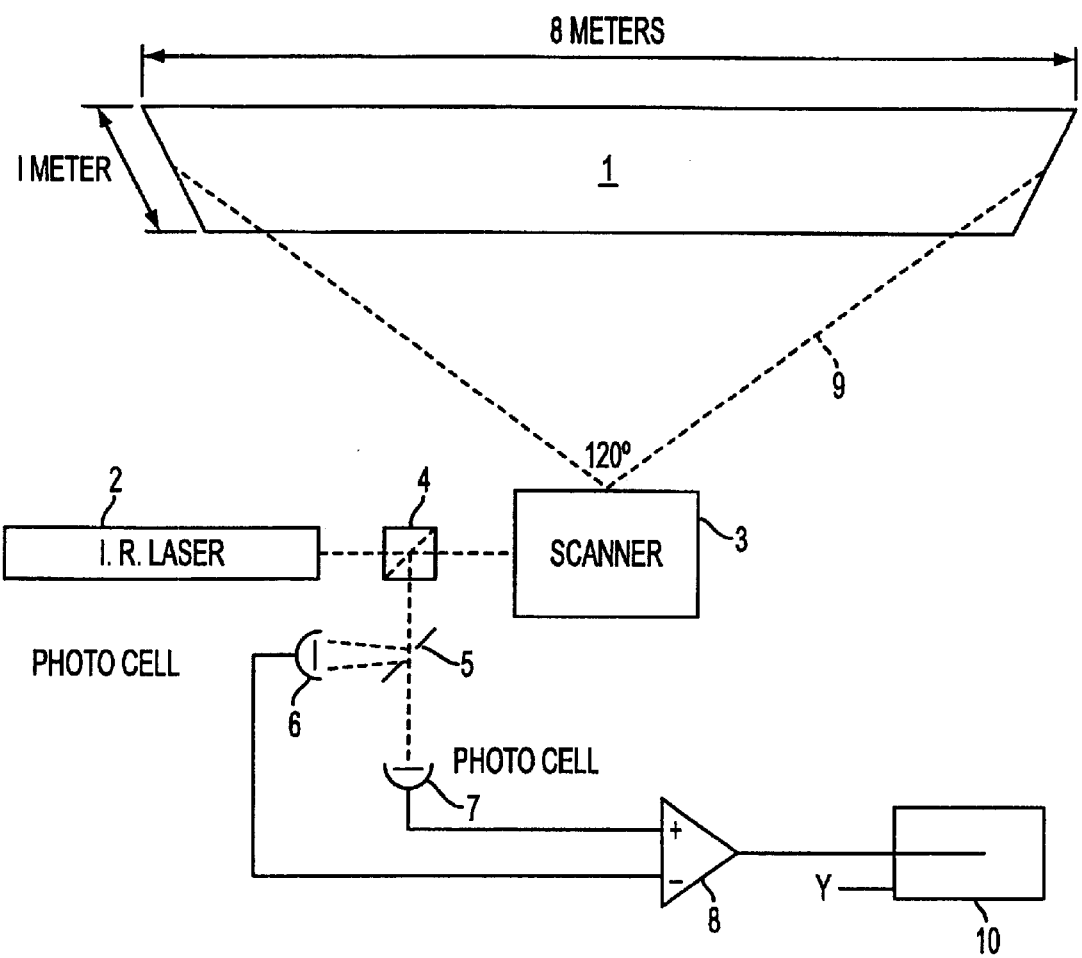
FIG. 1 shows diagrammatically in block shape a first embodiment of the device according to the invention, operating according to the scanning principle.

FIG. 1 shows a first embodiment of the device, in which said retroreflection can be determined. In FIG. 1, 1 indicates an area of observation, from which persons can view a visible object. In the close vicinity of said object not shown in the drawing, a first measuring arrangement according to the invention is mounted. It has a radiation source 2, preferably a source of invisible radiation, since visible radiation might undesirably attract attention, or hinder it. The radiation should not be focussed too strong, and also the radiation capacity must be low, in order to prevent possible damage to the eyes. A scanning member 3 receives the radiation beam and deflects it in the direction of the area of observation 1. In doing so, a scanning movement is made across 120° in the example shown, in one or more directions, as a result of which subsequently the total area of observation is covered by the radiation beam. The scanning member 3 can be a mechanical or opto-mechanical scanner, e.g. one that operates with a polygonal mirror wheel and a servo mirror, or an electronic or opto-electronic scanner, or otherwise.

Between the radiation source 2 and the scanning member 3 there is a partly transmitting deflection member 4, deflecting the returning, reflected radiation to a detector system, consisting of a centrally bored, e.g. 45° deflection member 5, a first detector 6 for receiving deflected radiation, and a second detector 7 for receiving radiation transmitted through the central bore of the deflection member. The outputs of the first detector 6 and the second detector 7 are connected to both inputs of a differential amplifier 8.

Said device operates as follows. The radiation source emits a focussed measuring beam to the scanning member 3, its output radiation beam 9 scanning the area of observation 1 across e.g. 120°. The radiation reflected there returns to the scanner and according to the path of the radiation source it goes to the partly transmitting deflection member 4 deflecting the reflected radiation to the centrally bored e.g. 45° deflection member 5. Owing to this, e.g. coaxial radiation will pass through the bore to the detector 7, whereas non-coaxial radiation will be reflected to the detector 6 by the deflection member 5. Thus, one can efficiently make a division between e.g. coaxial radiation and non-coaxial radiation, in the sense, that substantially non-coaxial radiation is able to reach the detector 6. The e.g. coaxially reflected radiation is now a standard for retroreflection at eyes in the area of observation and in this way, one can divide between coaxially and non-coaxially reflected radiation. Since the detector, apart from coaxial radiation, also receives non-coaxial radiation, the outputs of both detectors are connected to the inputs of a substracting member, in the illustrated embodiment shown as differential amplifier 8. The output signal of said differential amplifier can be processed further, e.g. by suitable computer programs. In the illustrated embodiment, this is indicated diagrammatically by the comparator circuit 10, in which said output signal is compared to a reference signal Y. In this way, signals can be obtained which are indicative of the attention persons give an object to be evaluated.

Another possibility is employing non-visible pulse radiation, and recording systems.

Figure 2:
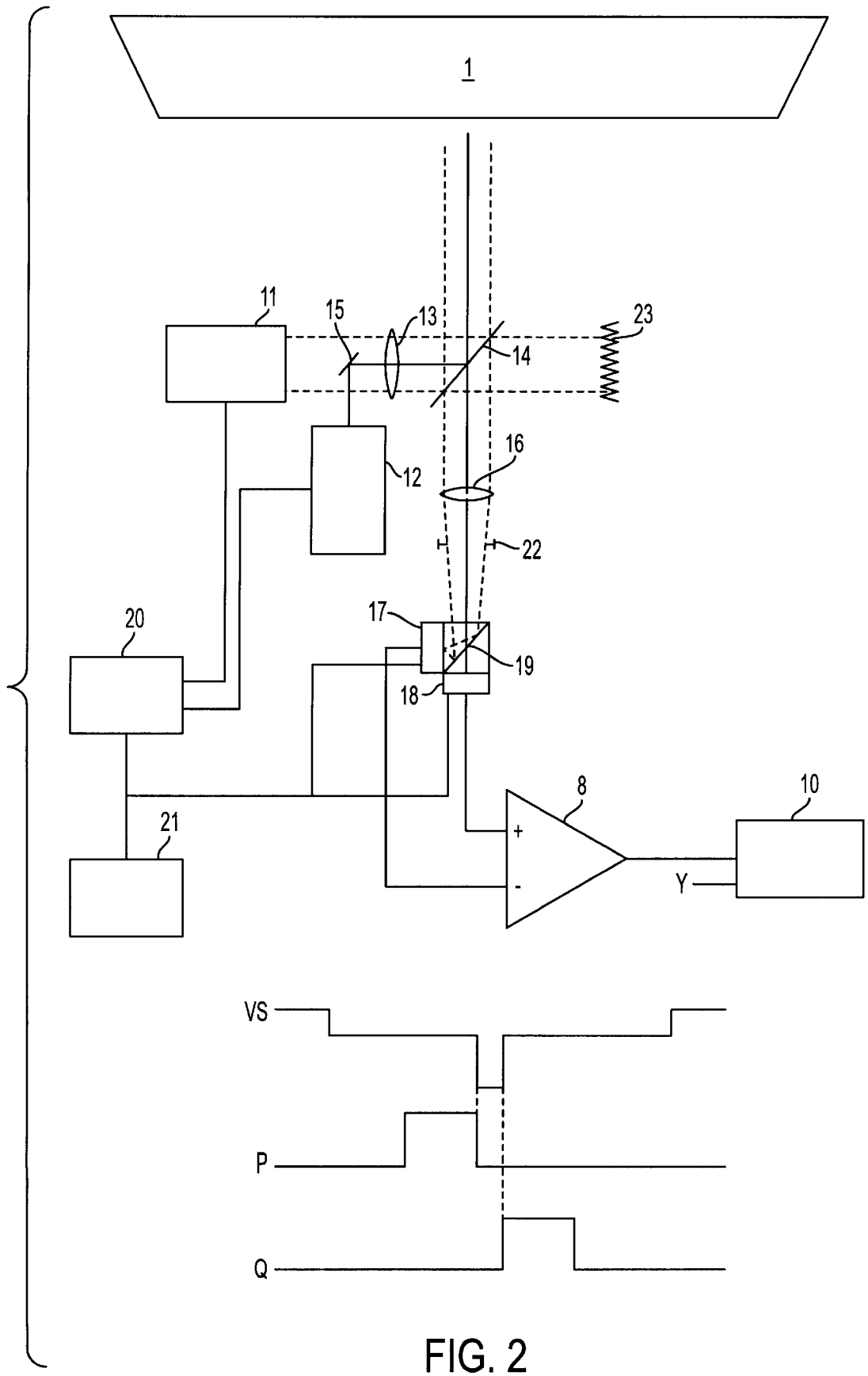
FIG. 2 shows a second embodiment of the device according to the invention, operating with the help of image recordings.

An example of such a device is shown in FIG. 2. There, 11 indicates a first pulse source (infrared) and 12 indicates a second pulse source. The radiation of the first pulse source 11 travels through an optical element 13 to a partly transmitting deflection member 14, in order to deflect the radiation to the area of observation 1. Through a deflection member 15 between said first pulse source and said optical element 13, the radiation of the second pulse source 12 is deflected into the direction of said optical element. Radiation reflected at the area of observation returns through the partly transmitting deflection member 14 and through an optical element 16, it reaches a recording system comprising a laterally arranged first recording unit 17, a transversely arranged second recording unit 18 and a beam splitter 19, splitting the reflected incident beam into two partial beams, reaching the respective recording units 17 and 18. In this embodiment, both recording units have one common optical element 16. The outputs of both recording units are in turn connected to a substracting circuit, shown as differential amplifier 8. Both pulse sources are connected to an electronic switch 20, e.g. a bistable vibrator. A sync pulse generator 21 is at one side connected to the electronic switch 20, at the other side to both recording units 17 and 18.

Said device operates as follows: the first pulse source 11 transmits non-coaxial, non-focussed pulses, synchronous to the recording time of said first recording unit 18. The sync pulse generator 21 controls this working in such a way, that opening and closing of the respective recording units 17 and 18 occurs in succession. There, the generator 21 generates vertical synchronizing pulses VS, an example of which being indicated at the bottom of the drawing. Said synchronizing pulses VS are applied to the first and second recording unit 17 and 18, respectively. These are set in such a way, that e.g. a valve is opened under the control of a falling and rising flank of said synchronizing pulse, respectively. Opening and closing of e.g. a valve of the first and second recording units, respectively, takes place under control of e.g. a clock signal synchronized with the synchronizing signal VS. Through the electronic switch 20, such working takes place in order to control the pulse sources 11 and 12 synchronously with the recording units 17 and 18.

In this way, it is achieved, that recording unit 17 can only receive radiation from the non-coaxial radiation source 12. However, retroreflection in the area of observation is only possible with the coaxial radiation of radiaton source 12, and recording unit 18 makes recordings, in which the eyes of persons or animals viewing are depicted extremely bright; so-called brightness pupils. On the other hand, recording unit 17 does not receive said brightness pupils, and by subtracting the outputs of recording units 17 and 18 in the differential amplifier 8, an output image signal exclusively or substantially consisting of brightness pupils is obtained. Since persons or animals not watching straight at the object can cause some "brightness" as well, it is necessary, that the signals obtained are further screened on relevance, which can be effected by suitable computer processing. In the drawing, this is illustrated diagrammatically by the comparator circuit 16.

Further, in FIG. 2, a limitation, e.g. a diaphragm, 22 is illustrated, which functions to adjust the beam of reflected radiation to the diameter of the optical element 13 of the incident radiation. Further, 23 indicates a radiation dimmer for excluding lateral reflection effects.

Figure 3:
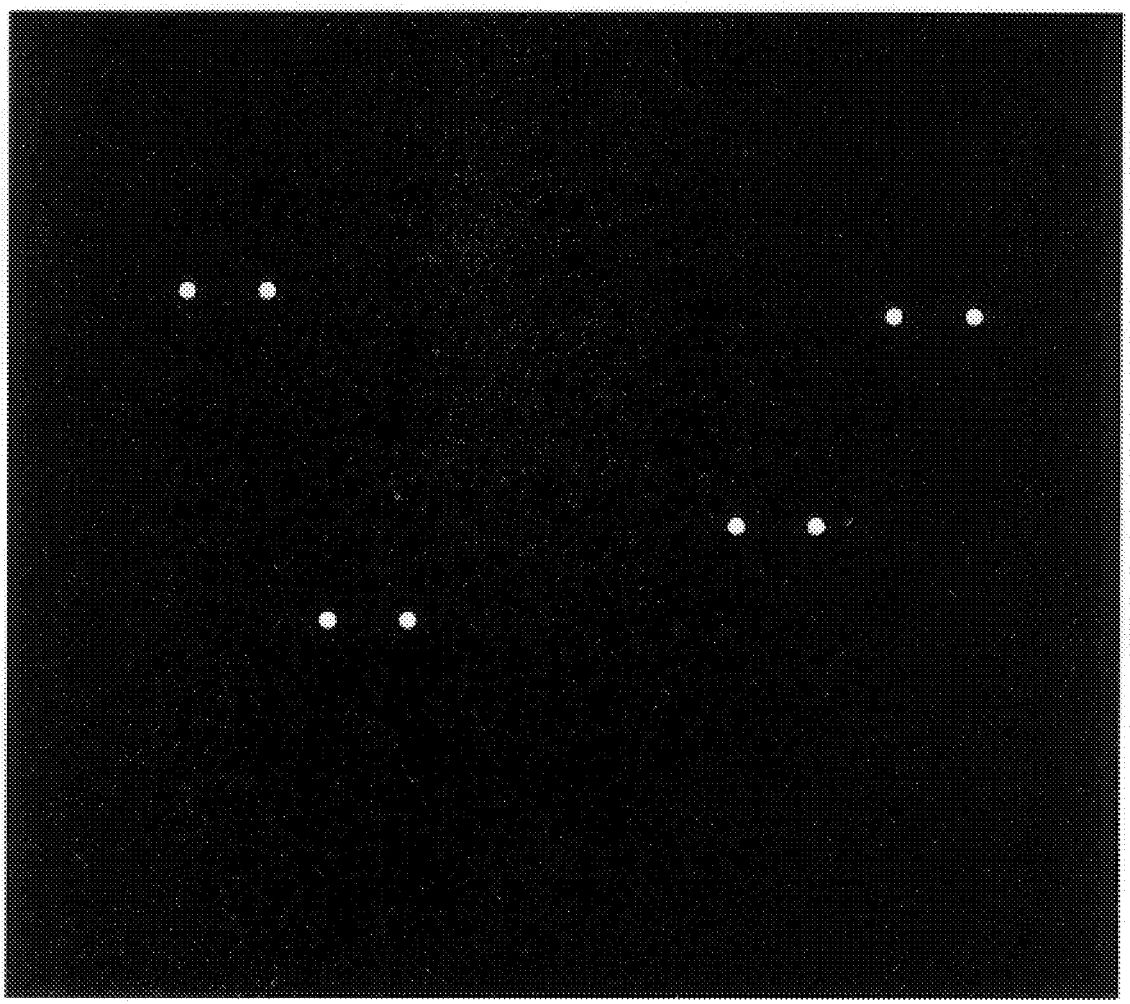
FIG. 3 shows a recording of "brightness" pupils obtained by said device.

FIG. 3 shows a recording obtained with such a device, in which the pairs of dots represent the so-called brightness pupils. It will be obvious, that viewing data can be obtained from such data.

Figure 4:
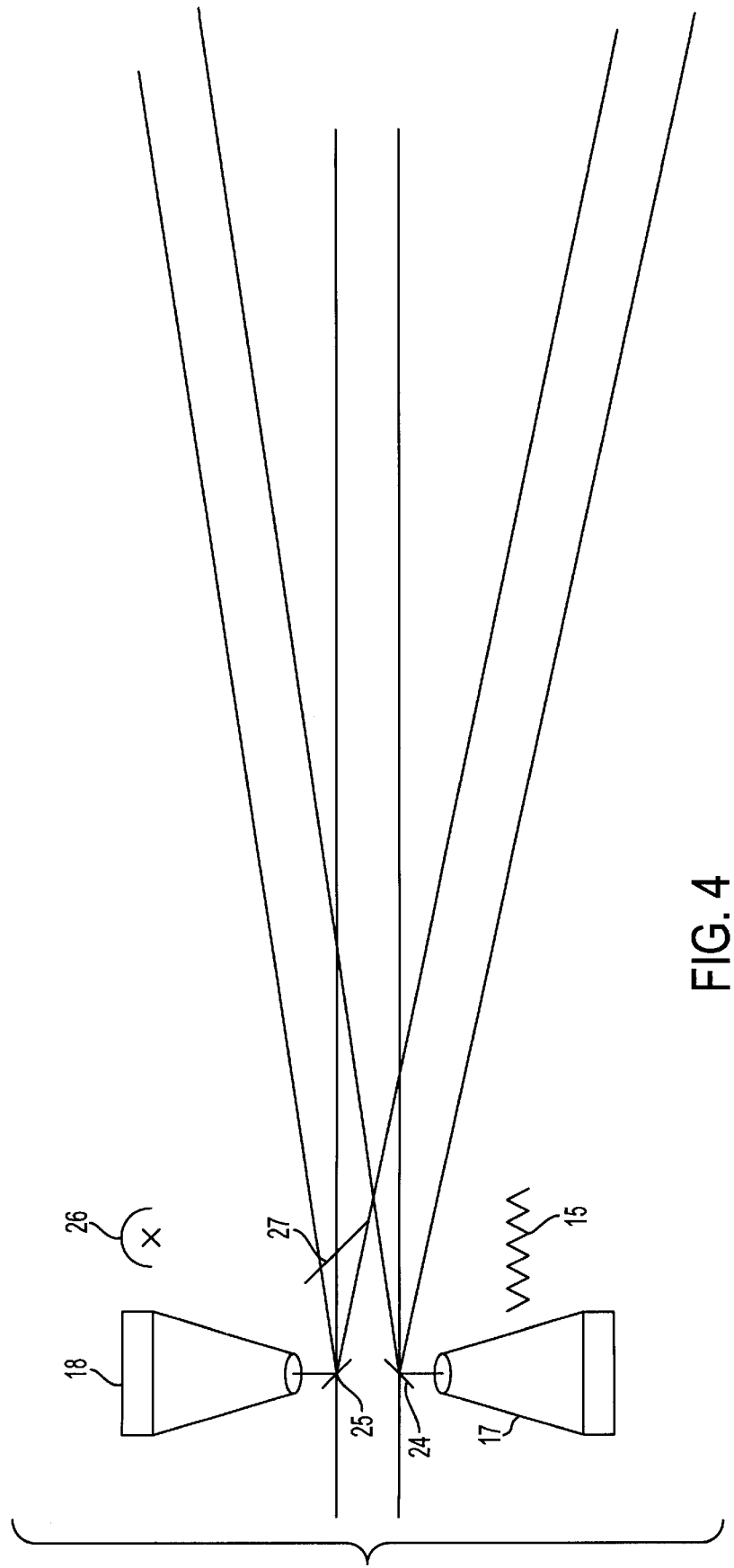
FIG. 4 shows a third embodiment of the device according to the invention, also operating with image recording.

FIG. 4 is a simplified embodiment of the device according to the invention, in which two recording units and one single pulse source are employed. There, both recording units 17 and 18 are arranged at a distance of at least 6 mm opposite each other with their receiving openings facing each other. Deflection members 24 and 25 provide for the radiation paths of the recording units are led to the area of observation 1, said radiation paths being slightly displaced in relation to each other. A partly transmitting deflection member 27 is arranged on the axis of the radiation path of recording unit 18, e.g. at an angle of 45° in relation to the axis direction of the radiation path of said recording unit. A pulse source 26, preferably of invisible radiation, is arranged next to the recording unit 18 in such a way, that through the deflection member 27, its radiation is deflected according to the direction of the radiation path of said recording unit. The pulse source 26 is synchronized with both recording units 17 and 18 in a way not indicated.

This device is based on the principle, that only the recording unit 18 is capable of receiving retroreflected radiation from the area of observation 1, which is not possible with the recording unit 17, since the latter has no suitable arrangement relation with pulse source 26 to that end. Therefore, apart from its ability to receive background radiation, the second recording unit 18 is also capable of receiving radiation of brightness pupils, such as e.g. coaxial retroreflection, whereas the first recording unit 17 receives background radiation only. The outputs of both recording units 17 and 18 are in turn coupled to a subtraction circuit not shown, by which, just like with the device of FIG. 2, recordings can be obtained, that show brightness pupils only, which can be taken as a standard for the public watching the object. In this case too, it can be necessary to dim the radiation with the help of a radiation dimmer 15.

In the above, the invention has been explained by way of a number of examples. However, it will be obvious, that the invention is not limited to these specific examples, nor to the principle of retroreflection, but that there are many possibilities for applying the invention. A number of those have been discussed in the first part of the descriptive portion. Further embodiments and possibilities will be clear to the expert by way of description and claims.

I claim:

1. A device for measuring the visual attention of persons or animals for an object, comprising:

a radiation member for supplying radiation;

a scanning member, scanningly guiding the radiation of the radiation member across an area of observation;

a detector member, said detector member having a beam separator, including a reflector unit mounted therein, arranged at an angle in relation to a beam path of radiation reflected from the area of observation and having at least two detectors mounted for receiving the radiation transmitted by said beam separator and the radiation reflected by said beam separator, respectively; and a subtracting member having respective inputs electrically connected to respective outputs of said at least two detectors.

2. The device according to claim 1, wherein said detector member includes a reflector unit mounted therein, and a central passage for passing coaxial radiation.

3. A device according to claim 2, further comprising a partly transmitting deflection member mounted at an angle in the radiation path between said radiation member and said scanning member, said partly transmitting deflection member deflecting the returning reflected radiation towards said detector member.

4. The device according to claim 1, further comprising a partly transmitting deflection member mounted at an angle in the radiation path between said radiation member and said scanning member, said partly transmitting deflection member deflecting the returning reflected radiation towards said detector member.

5. The device according to claim 1, wherein an output of said subtracting circuit is connected to one input of a comparator circuit, with a reference signal being connected to an other input of said comparator circuit.

6. A method for measuring the visual attention of persons or animals for an object, comprising:

a) transmitting, from a position near the object, at least one beam of radiation from at least one radiation member into an area of observation where moving persons or animals are present;

b) detecting radiation reflected from the area of observation with at least one signal detector member;

c) arranging said at least one radiation member and said at least one signal detector member to distinguish coaxial radiation reflected from the area of observation from non-coaxial radiation reflected from the area of observation; and d) transforming the coaxial radiation, indicative of radiation reflected at the retina and/or the cornea of eyes of the moving persons or animals, into an evaluation signal.

7. The method according to claim 6, wherein said transmitting step includes scanning the at least one beam of radiation across the area of observation, the at least one beam of radiation being a substantially parallel beam.

8. The method according to claim 6, wherein the at least one beam of radiation is a pulsed beam, transmitted according to pulse cycles into the area of observation.

9. A device for measuring the visual attention of persons or animals for an object, comprising:

a signal recording system for receiving radiation reflected from an area of observation where persons or animals are present;

a radiation pulse system, synchronized to said signal recording system, for pulsewise irradiation of the area of observation; and means for distinguishing, in signals recorded in said signal recording system, radiation reflected by a retina or a cornea of eyes of persons or animals in the area of observation from radiation reflected by other objects in the area of observation.

10. The device according to claim 9, wherein said signal recording system includes one recording unit, and said radiation pulse system includes one pulse source of radiation having its pulse time synchronized with the recording time of said signal recording system, said pulse source of radiation being arranged transversely to the radiation path between recording optics and the area of observation, a partly transmitting deflection member being positioned in the radiation path, said partly transmitting deflection member deflecting the radiation of said pulse source of radiation in the direction of the radiation path to the area of observation.

11. The device according to claim 9, wherein said signal recording system includes one recording unit, and said radiation pulse system includes a first pulse source and a second pulse source, having their pulse times alternately synchronized with the recording time of said signal recording system, said first pulse source being arranged relative to said signal recording system for irradiating the area of observation with radiation being non-coaxial to the radiation path between recording optics and the area of observation, and said first pulse source being arranged transversely to a radiation path in which a first deflection member has been positioned, said first deflection member deflecting the radiation of said second pulse source in the direction of the radiation path to the area of observation, and wherein said device further comprises a subtracting circuit, coupled to the output of said signal recording system, said subtracting circuit subtracting subsequently recorded signals.

12. The device according to claim 11, wherein said first deflection member is positioned in the radiation path of said first pulse source and deflects radiation of said second pulse source into the radiation path of said first pulse source, and wherein said device further comprises a second deflection member positioned in the radiation path between the area of observation and said one recording unit to deflect radiation from said first or second pulse sources to the area of observation.

13. The device according to claim 11, further comprising a comparator circuit, and wherein an output of said subtracting circuit is connected to one input of said comparator circuit, with a reference signal being connected to an other input of said comparator circuit.

14. The device according to claim 9, wherein said signal recording system has a first recording unit and a second recording unit, arranged at a short distance from each other in such a way that the radiation path between the area of observation and said first recording unit is slightly shifted in relation to that which is between the area of observation and said second recording unit, said radiation pulse system having one pulse source, its pulse time being synchronized with the recording time of said first and second recording units, said radiation pulse system being arranged transversely to the radiation path between the area of observation and said first recording system, wherein said device further comprises a partly transmitting deflection member mounted in the radiation path, said partly transmitting deflection member deflecting the pulse source radiation in the direction of the radiation path to the area of observation, and wherein said device further comprises a subtracting circuit having respective inputs electrically connected to respective outputs of said first and second recording units.

15. The device according to claim 14, wherein, together with a beam separator, said first and second recording units positioned at an angle to each other form said signal recording system having a common radiation path between the area of observation and said signal recording system.

16. The device according to claim 14, further comprising a comparator circuit, and wherein an output of said subtracting circuit is connected to one input of said comparator circuit, with a reference signal being connected to an other input of said comparator circuit.

17. The device according to claim 9, wherein said signal recording system includes a first recording unit and a second recording unit, and said radiation pulse system includes a first pulse source and a second pulse source, said first pulse source being synchronized with said first recording unit and said second pulse source being synchronized with said second recording unit such that alternately said first recording unit records radiation of said first pulse source reflected from the area of observation and said second recording unit records radiation of said second pulse source reflected from the area of observation, in which said first pulse source is positioned non-coaxially in relation to said signal recording system and provides a radiation beam that is not reflected coaxially from the area of observation to said first recording unit, and said second pulse source is positioned coaxially in relation to said signal recording system arrangement and provides a radiation beam that is reflected coaxially from the area of observation to said second recording unit, and wherein said device further comprises a subtracting circuit having respective inputs electrically connected to respective outputs of said first and second recording units.

18. The device according to claim 17, wherein, together with a beam separator, said first and second recording units positioned at an angle to each other form said signal recording system having a common radiation path between the area of observation and said signal recording system.

19. The device according to claim 17, further comprising a first deflection member positioned in the radiation path of said first pulse source, said first deflection member deflecting radiation of said second pulse source into the radiation path of said first pulse source, and further comprising a second deflection member positioned in the radiation path between the area of observation and said signal recording unit to deflect radiation from said first or second pulse sources to the area of observation.

20. The device according to claim 17, further comprising a comparator circuit, and wherein an output of said subtracting circuit is connected to one input of said comparator circuit, with a reference signal being connected to an other input of said comparator circuit.

21. The device according to claim 9, further comprising at least two discrete members in an integrated form.

22. The device according to claim 9, further comprising at least two optical components in an integrated form.

23. A device for measuring the visual attention of persons or animals for an object, comprising:

an irradiation system near the object for irradiating visible radiation into an area of observation where persons or animals are present;

at least one of a spectral sensitive signal recording system and a spectral selective signal recording system for receiving radiation radiated from said irradiation system and reflected at said area of observation, the radiation being reflected at the retina or cornea of eyes of persons or animals in the area of observation; and means for red analysis to distinguish the signals recorded in said signal recording system.

24. The device according to claim 23, further comprising at least two discrete members in an integrated form.

25. The device according to claim 23, further comprising at least two optical components in an integrated form.

* * * * *